United States Patent

Mitsuhashi et al.

Patent Number: 5,837,877
Date of Patent: Nov. 17, 1998

[54] PROCESS FOR PREPARING OPTICALLY ACTIVE 4-HYDROXY-2-PYRROLIDONE

[75] Inventors: Shigeru Mitsuhashi; Hidenori Kumobayashi, both of Hiratsuka, Japan

[73] Assignee: Takasago International Corporation, Tokyo, Japan

[21] Appl. No.: 790,931

[22] Filed: Jan. 29, 1997

[30] Foreign Application Priority Data

Feb. 2, 1996 [JP] Japan .................................. 8-039065

[51] Int. Cl.⁶ ............................................. C07D 207/273
[52] U.S. Cl. ............................................................ 548/544
[58] Field of Search ............................................. 548/544

[56] References Cited

U.S. PATENT DOCUMENTS 4,250,093  2/1981  Pesa et al. ........................ 548/544 X
5,276,164  1/1994  Laffan et al. ........................ 548/544

Primary Examiner—Michael G. Ambrose

Attorney, Agent, or Firm—Sughrue, Mion, Zinn, Macpeak & Seas, PLLC

[57] ABSTRACT

A process for preparing optically active 4-hydroxy-2-pyrrolidone comprising asymmetrically hydrogenating an N-substituted-4-amino-3-oxobutanoic ester represented by formula (I):

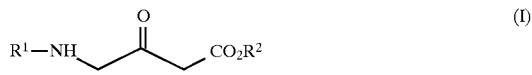

wherein $R^1$ represents a benzyloxycarbonyl group, the benzene ring of which may be substituted; and $R^2$ represents a lower alkyl group having 1 to 4 carbon atoms, in the presence of a ruthenium-optically active phosphine complex as a catalyst to obtain an optically active N-substituted-4-amino-3-hydroxybutanoic ester, deblocking, and cyclizing the ester. A series of the reactions can be carried out in one pot. Optically active 4-hydroxy-2-pyrrolidone is obtained in high yield with high optical purity, and is useful in the synthesis of carbapenem antibiotics

4 Claims, No Drawings

PROCESS FOR PREPARING OPTICALLY ACTIVE 4-HYDROXY-2-PYRROLIDONE

FIELD OF THE INVENTION

This invention relates to a process for preparing optically active 4-hydroxy-2-pyrrolidone useful as a starting material for synthesizing pharmaceuticals.

BACKGROUND OF THE INVENTION

Optically active 4-hydroxy-2-pyrrolidone is known as an important intermediate for synthesizing carbapenem antibiotics (see JP-A-1-207266, the term "JP-A" as used herein means an "unexamined published Japanese patent application"), and an economical process for preparing the compound has been desired.

Conventional processes for preparing optically active 4-hydroxy-2-pyrrolidone include (1) a process comprising reducing a γ-amino-3-oxobutanoic ester with its amino group protected by a known method (*Synthesis*, pp. 403–408 (1992)) with bread's yeast, hydrolyzing the resulting optically active γ-amino-3-hydroxybutanoic ester with its amino group protected, followed by deblocking to obtain γ-amino-3-hydroxybutanoic acid (GABOB), and cyclizing the acid with hexamethyldisilazane (*Synthesis*, pp. 614–616 (1978)) and (2) a process comprising reducing 4-chloro-3-oxobutanoic ester with bread's yeast and cyclizing the resulting optically active alcohol by the action of ammonia (*J. Chem. Res., Synop.*, No. 4, pp. 132–133 (1984)).

Known processes for preparing racemic 4-hydroxy-2-pyrrolidone include (3) a process comprising synthesizing 4-chloro-3-hydroxybutanoic ester by a known method (JP-A-57-183749), hydrolyzing the ester to obtain the corresponding carboxylic acid, and cyclizing the carboxylic acid by a known method in the literature (*Tetrahedron Letters*, Vol. 211, pp. 2443–2446 (1980)) and (4) a process comprising protecting the hydroxyl group of a 4-chloro-3-hydroxybutanoic ester by esterification with a lower carboxylic acid and cyclizing the protected ester with ammonia (JP-A-57-183756 and JP-A-61-176564).

Process (1), which uses reduction with yeast as a means for obtaining an optically active compound, is disadvantageous for production efficiency in that the solvent required is about 100 times as much as the reaction substrate and that yeast is used 4 times as much as the substrate. In addition the cyclization step requires a special reagent.

Process (2) uses reduction with yeast for obtaining an optically active compound and is therefore disadvantageous for production efficiency. Cyclization of the 4-chloro-3-oxobutanoic ester must be done with a large excess of ammonia, requires a pressure container, and is accompanied by considerable by-production, making purification and isolation of 4-hydroxy-2-pyrrolidone complicated.

Process (3) uses alumina or silica gel as a catalyst for cyclization to obtain a desired compound. The yield attained is low.

Process (4), in which a 4-chloro-3-hydroxybutanoic ester with its hydroxyl group protected is reacted with ammonia to obtain a cyclized product, involves complicated steps and requires a pressure container and is therefore disadvantageous for industrial application.

SUMMARY OF THE INVENTION

In the light of the above-mentioned present situation, the inventors of the present invention have conducted extensive study on an effective and economically excellent process for preparing optically active 4-hydroxy-2-pyrrolidone. As a result, they have found an inexpensive and practical process and thus reached the invention.

The invention relates to a process for preparing optically active 4-hydroxy-2-pyrrolidone represented by formula (III):

comprising asymmetrically hydrogenating an N-substituted-4-amino-3-oxobutanoic ester represented by formula (I):

wherein $R^1$ represents a benzyloxycarbonyl group, the benzene ring of which may be substituted; and $R^2$ represents a lower alkyl group having 1 to 4 carbon atoms, in the presence of a ruthenium-optically active phosphine complex as a catalyst to obtain an optically active N-substituted-4-amino-3-hydroxybutanoic ester represented by formula (II):

wherein $R^1$ and $R^2$ are as defined above; and * indicates an asymmetric carbon atom, deblocking, and cyclizing the ester.

Specifically, the invention provides a process for preparing optically active 4-hydroxy-2-pyrrolidone of formula (III) in high yield without reducing the optical purity, which comprises asymmetrically hydrogenating a β-keto ester (N-substituted-4-amino-3-oxobutanoic ester (I)) in the presence of a catalytic amount of a ruthenium-optically active phosphine complex to obtain an optically active (3R)- or (3S)-N-substituted-4-amino-3-hydroxybutanoic ester (II) at a high enantiomer selectivity, deblocking the optically N-substituted-hydroxybutanoic ester (II) (a benzyloxycarbonyl group, for instance, is removed by hydrolysis in the presence of a palladium-on-carbon catalyst), and cyclizing the deprotected compound by heating in an alcohol without isolation.

DETAILED DESCRIPTION OF THE INVENTION

The starting β-keto ester (I) is synthesized from easily available N-protected glycine by a known process described, e.g., in Nishi, et al., *Journal of Antibiotics*, Vol. 47, p. 357 (1994).

The amino protecting group in the β-keto ester (I) as represented by $R^1$ is a benzyloxycarbonyl group, the benzene ring of which may be substituted. The substituent on the benzene ring includes a lower alkyl group having 1 to 4 carbon atoms (preferably a methyl group or a t-butyl group), a lower alkoxy group having 1 to 4 carbon atoms (preferably a methoxy group), and a halogen atom (preferably a chlorine atom). Examples of the substituted benzyl group are p-methoxybenzyl, 2,4-dimethoxybenzyl, p-methylbenzyl, 3,5-dimethylbenzyl, p-chlorobenzyl, and p-t-butylbenzyl.

$R^2$ in the β-keto ester (I) is a lower alkyl group having 1 to 4 carbon atoms.

The asymmetric hydrogenation of the β-keto ester (I) can be carried out in the presence of a catalytic amount of a ruthenium-optically active phosphine complex in a solvent, e.g., an alcohol, under a hydrogen pressure, e.g., of 5 to 100 atm at a temperature, e.g., of 10° to 100° C., for a period, e.g., of 5 to 20 hours.

The protective group of the resulting optically active protected N-substituted-4-amino-3-hydroxybutanoic ester is then deblocked by addition of a deblocking catalyst to the hydrogenation reaction mixture, and the reaction mixture is then subjected to cyclization to obtain optically active 4-hydroxy-2-pyrrolidone.

In the present invention, the asymmetric hydrogenation of the β-keto ester (I) and the subsequent deblocking and cyclization can be carried out in one pot in the same solvent without isolating and purifying the intermediate product. Therefore, the desired compound can be obtained in a high yield. This one-pot synthesis system is a highly advanced and practical process.

The ruthenium-optically active phosphine complex which can be used as a catalyst for asymmetric hydrogenation includes a compound represented by formula (IV):

$$Ru_xH_yCl_z(BINAP)_2(S)_p \qquad (IV)$$

wherein BINAP stands for 2,2'-bis(diphenylphosphino)-1,1'-binaphthyl; S represents a tertiary amine; y represents 0 or 1; when y is 0, x represents 2, z represents 4, and p represents 1; and when y is 1, x represents 1, z represents 1, and p represents 0, a compound represented by formula (V):

$$[RuH_l(BINAP)_v]Y_w \qquad (V)$$

wherein BINAP is as defined above; Y represents $ClO_4^-$, $BF_4^-$ or $PF_6^-$; l represents 0 or 1; when l is 0, v represents 1, and w represents 2; and when l is 1, v represents 2, and w represents 1, and a compound represented by formula (VI):

$$[RuX_t(S)_m(BINAP)]Y_n \qquad (VI)$$

wherein BINAP is as defined above; S represents benzene which may be substituted with a straight-chain or branched lower alkyl group or a carboalkoxy group, or acetonitrile; X represents a halogen atom; Y represents a halogen atom, $ClO_4^-$, $BF_4^-$, $PF_6^-$ or $BPh_4^-$, wherein Ph represents a phenyl group; l represents 1 or 0; when l is 1, m represents 1, and n represents 1; and when l is 0, m represents 4, and n represents 2.

The compounds of formulae (IV) and (V) are disclosed in JP-B-6-99367 (the term "JP-B" as used herein means an "examined Japanese patent publication"), and the compounds of formula (VI) are disclosed in JP-B-7-57758.

BINAP in these ruthenium-optically active phosphine complexes embraces optical isomers, i.e., (R)-BINAP and (S)-BINAP An appropriate choice of the isomer is made according to the absolute configuration of a desired compound. That is, (R)-BINAP is to be used for the preparation of an (S)-compound, and (S)-BINAP for an (R)-compound.

The ruthenium-optically active phosphine complex is used at a molar ratio of 1/100 to 1/10000, preferably 1/500 to 1/1000, to the β-keto ester (I) as a reaction substrate.

As the solvents for the hydrogenation reaction, they are not particularly limited as far as they don't hinder the reaction, and specific examples of the solvents include alcohols such as methanol, ethanol, propanol, and isopropanol; aromatic hydrocarbons such as benzene, toluene, and xylene; ethers such as diethyl ether, diisopropyl ether, dioxane, and tetrahydrofuran; halogenated hydrocarbons such as chloroform, dichloromethane, and 1,1,2,2-tetrachloroethane; and esters such as ethyl acetate. These solvents can be used singly or in combination in an appropriate proportion. Of these, alcohols are particularly preferred. It is preferable to use an alcohol solvent having the same alcoholic residue as that contained in the hydrogenation substrate. The solvent is usually used 2 to 5 times (volume/weight) as much as the substrate.

Deblocking of the optically active N-substituted-4-amino-3-hydroxybutanoic (II) can be carried out by, for example, hydrogenolyzing the ester (II) in the presence of a palladium-on-carbon catalyst at a hydrogen pressure of 1 to 30 atm and at 15° to 40° C. for 0.5 to 8 hours. As the solvents for the deblocking reaction, they are not particularly limited as far as they don't hinder the reaction, and specific examples of the solvents include alcohols such as methanol, ethanol, propanol, and isopropanol. It is particularly preferable to use the same solvent as that used for the hydrogenation reaction described above. The solvent is usually used 2 to 5 times (volume/weight) as much as the substrate.

Cyclization of the resulting non-protected compound can be conducted by heating usually at 40° to 70° C., preferably 50° to 65° C. After the cyclization, the resulting crude product of optically active 4-hydroxy-2-pyrrolidone is purified by dissolution, crystallization and filtration to give optically active 4-hydroxy-2-pyrrolidone in high yield and with high optical purity.

According to the invention, there is presented a novel process for preparing optically active 4-hydroxy-2-pyrrolidone which involves no complicated steps. The process according to the invention provides optically active 4-hydroxy-2-pyrrolidone in high yield and with high optical purity.

The invention will now be illustrated in greater detail with reference to Examples, but it should be understood that the invention is not limited thereto.

Equipment and instruments used for measurement of physical properties of the products prepared and the conditions of measurement were as follows unless otherwise specified.

Nuclear Magnetic Resonance Spectrum ($^1$H-NMR):
Model AM-400 (400 MHz), manufactured by Bruker Inc.
Internal standard: tetramethylsilane
Melting point: Model MP-S3 (Yanagimoto Syoji K.K.)
Optical Purity:
Hitachi Liquid Chromatography L-6000 (manufactured by Hitachi, Ltd.)
Column: Chiralpak-AD; 4.6 mm×250 mm (manufactured by Daicel Chemical Industries, Ltd.)
Solvent: hexane/ethanol/methanol=95/5/3 (by volume)
Flow Rate: 0.8 ml/min
Detection: 215 nm

REFERENCE EXAMPLE 1

Synthesis of Ethyl 4-Benzyloxycarbonylamino-3-oxobutanoate

In a 1000 ml four-necked flask were charged 50 g (0.239 mol) of N-benzyloxycarbonyl-glycine and 300 ml of acetonitrile in a nitrogen stream, and 39.54 g (0.2438 mol) of 1,1'-carbonyldiimidazole was added thereto over a period of about 30 minutes, whereupon evolution of carbonic acid gas was observed. The reaction mixture was stirred at room temperature (22° to 24° C.) for 2 hours. After cooling to 7° C., 61.0 g (0.359 mol) of potassium ethyl malonate was added thereto over a 5-minute period, and 22.98 g (0.241 mol) of magnesium chloride was added over a 30-minute period, whereupon evolution of carbonic acid gas was observed. The reaction mixture was stirred at room temperature for 30 minutes and then at 50° C. for an addition period of 2 hours to complete the reaction.

Acetonitrile was about 80% removed by evaporation under reduced pressure, and 550 ml of a 5% hydrochloric acid aqueous solution was added to the residue. The mixture was extracted with 180 ml of butyl acetate. The organic layer was washed with 100 ml of a 5% hydrochloric acid aqueous solution, neutralized with 100 ml of a 8% sodium hydrogencarbonate aqueous solution, and washed with 100 ml of water. The solvent was evaporated under reduced pressure to give 67.1 g of the title compound as liquid.

An aliquot of the product was isolated and purified to find that the yield was 90.3%.

$^1$H-NMR (400 MHz, CDCl$_3$) δ ppm: 1.26 (3H, t, J=7.1 Hz), 3.46 (2H, s), 4.15 to 4.2 (4H, m) 5.1 (2H, s), 5.63 (1H, s), 7.27–7.34 (5H, m).

EXAMPLE 1

(1) Synthesis of Ethyl (3S)-4-Benzyloxycarbonylamino-3-hydroxybutanoate

In a 200 ml autoclave were put 40 g of the product obtained in Reference Example 1 (containing 35.9 g (0.129 mol) of ethyl 4-benzyloxycarbonylamino-3-oxobutanoate), 120 ml of ethanol, and 0.173 g (0.102 mmol) of Ru$_2$Cl$_4$((R)-BINAP)$_2$.NEt$_3$ in a nitrogen stream, and asymmetric hydrogenation was conducted at a hydrogen pressure of 30 atm at 50° C. for 17 hours (conversion: 98.4%; optical purity: 94.0% e.e.).

Ethanol was evaporated under reduced pressure to give 38.9 g of the title compound as liquid.

An aliquot of the product was isolated and purified by column chromatography to find that the yield was 90.5%.

$^1$H-NMR (400 MHz, CDCl$_3$) δ ppm: 1.26 (3H, t, J=7.1 Hz), 2.41–2.47 (2H, m), 3.14–3.4 (2H, m), 4.09 to 4.2 (4H, m), 5.09 (2H, s), 5.48 (1H, s), 7.27–7.34 (5H, m)

The optical purity was determined under the following conditions:

Column: Chiralcel OD-H; 4.6 mm×250 mm (manufactured by Daicel Chemical Industries, Ltd.)

Solvent: hexane/isopropyl alcohol=9/1 (by volume)

Flow Rate: 1.0 ml/min

Detection: 210 nm (2) Synthesis of (S)-4-Hydroxy-2-pyrrolidone

In a 200 ml autoclave were charged 33.5 g of the product obtained in (1) (containing 28.16 g (0.1 mol) of ethyl (3S)-4-benzyloxycarbonylamino-3-hydroxybutanoate), 100 ml of methanol, and 1.68 g of wet 5% palladium-on-carbon, and hydrogenolysis was conducted at 25° C. under a hydrogen pressure of 4 to 6 atm for 3.5 hours. The reaction mixture was filtered, and methanol was evaporated under reduced pressure to obtain 18.95 g (liquid) of a crude aminohydroxy-ester. A 17 g portion of the crude product was weighed out, and 85 ml of methanol was added thereto, followed by stirring at 60° C. for 8 hours and then at room temperature for 7 hours to conduct cyclization. One gram of activated carbon was added to the reaction mixture, and the mixture was stirred at 50° C. for 1 hour, followed by filtration. For the filtration, 20 ml of methanol was used. The methanolic filtrate was crystallized by stirring at −15° C. for 1.5 hours. The crystals were collected by filtration and washed with ethyl acetate/methanol (4/1) to obtain 6.03 g of first crystals. To the first mother liquor (6.83 g) was added 17 ml of methanol, and the methanolic solution was crystallized in the same manner as above to obtain 2.07 g of second crystals. The first crystals and the second crystals were combined to give 8.1 g (89.3%) of the title compound.

Melting point: 158°–162° C.

Optical purity: 100% e.e.

$^1$H-NMR (400 MHz, D$_2$O) δ ppm: 2.26 (1H, dd, J=2 Hz, 18 Hz), 2.75 (1H, dd, J=6.4 Hz, 17.6 Hz), 3.32 (1H, dd, J=1.6 Hz, 11.6 Hz), 3.7 (1H, dd, J=5.2 Hz, 11.6 Hz), 4.59–4.62 (1H, m)

EXAMPLE 2

Synthesis of (S)-4-Hydroxy-2-pyrrolidone (One-pot Reaction)

In a 200 ml autoclave were charged 40 g of the product obtained in Reference Example 1 (containing 35.9 g (0.129 mol) of ethyl 4-benzyloxycarbonylamino-3-oxobutanoate), 120 ml of ethanol, and 0.179 g (0.204 mmol) of [RuCl(benzene)((R)-BINAP)]Cl in a nitrogen stream, and asymmetric hydrogenation was conducted at 50° C. and at a hydrogen pressure of 30 atm for 17 hours (conversion: 98.2%; optical purity: 93.8% e.e.). Thereafter, 1.68 g of wet 5% palladium-on-carbon was put therein, and hydrogenolysis was carried out at 25° C. and at a hydrogen pressure of 4 to 6 atm for 4.5 hours. The reaction mixture was stirred at 60° C. for 8 hours and then at room temperature for 7 hours to carry out cyclization. To the reaction mixture was added 0.5 g of activated carbon, followed by stirring at 50° C. for 1 hour. To the mixture was added 20 ml of ethanol, and the mixture was filtered. The methanolic filtrate was crystallized by stirring at −10° C. for 1.5 hours, followed by filtration to obtain 10.4 g of the title compound in a yield of 80.1%.

Melting point: 158° to 162° C.

Optical purity: 100% e.e.

EXAMPLE 3

Synthesis of (S)-4-Hydroxy-2-pyrrolidone (One-pot Reaction)

In a 200 ml autoclave were charged 39.5 g of methyl 4-benzyloxycarbonylamino-3-oxobutanoate obtained in the same manner as in Reference Example 1 except for replacing potassium ethyl malonate with potassium methyl malonate (purity: 34.4 g (0.129 mol)), 120 ml of methanol, and 0.21 g (0.204 mmol) of [Ru(R)-BINAP)](PF$_6$)$_2$ in a nitrogen stream, and asymmetric hydrogenation was conducted at 50° C. and at a hydrogen pressure of 30 atm for 17 hours (conversion: 98.0%; optical purity: 91.6% e.e.). Thereafter, 1.68 g of wet 5% palladium-on-carbon was put therein, and hydrogenolysis was carried out at 25° C. and at a hydrogen pressure of 4 to 6 atm for 4.5 hours. The reaction mixture was stirred at 60° C. for 8 hours and then at room temperature for 7 hours to carry out cyclization. To the reaction mixture was added 0.5 g of activated carbon, followed by stirring at 50° C. for 1 hour. To the mixture was added 20 ml of ethanol, and the mixture was filtered. The methanolic filtrate was crystallized by stirring at −15° C. for 1.5 hours, followed by filtration to obtain 10.1 g of the title compound in a yield of 77.3%.

Melting point: 158° to 162° C.

Optical purity: 100% e.e.

EXAMPLE 4

Synthesis of (S)-4-Hydroxy-2-pyrrolidone (One-pot Reaction)

In the same manner as in Example 2, except for replacing N-benzyloxycarbonyl-glycine with N-p-methoxybenzyloxycarbonyl-glycine and replacing [RuCl(benzene)((R)-BINAP)]Cl with $RU_2Cl_4$(R)-BINAP).$NEt_3$, 10.5 g of the title compound was obtained in a yield of 80.3%.

Melting point: 158° to 162° C.

Optical purity: 100% e.e.

While the invention has been described in detail and with reference to specific examples thereof, it will be apparent to one skilled in the art that various changes and modifications can be made therein without departing from the spirit and scope thereof.

What is claimed is:

1. A process for preparing optically active 4-hydroxy-2-pyrrolidone represented by formula (III):

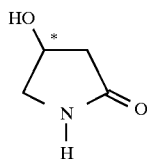   (III)

comprising asymmetrically hydrogenating an N-substituted-4-amino-3-oxobutanoic ester represented by formula (I):

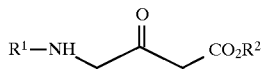   (I)

wherein $R^1$ represents a benzyloxycarbonyl group, the benzene ring of which may be substituted; and $R^2$ represents a lower alkyl group having 1 to 4 carbon atoms, in the presence of a ruthenium-optically active phosphine complex as a catalyst to obtain an optically active N-substituted-4-amino-3-hydroxybutanoic ester represented by formula (II):

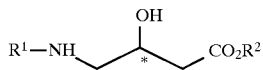   (II)

wherein $R^1$ and $R^2$ are as defined above; and * indicates an asymmetric carbon atom, deblocking, and cyclizing the ester.

2. The process according to claim 1, wherein the ruthenium-optically active phosphine complex is used at a molar ratio of 1/100 to 1/10000 to the N-substituted-4-amino-3-oxobutanoic ester represented by formula (I).

3. The process according to claim 1, wherein the ruthenium-optically active phosphine complex is used at a molar ratio of 1/500 to 1/1000 to the N-substituted-4-amino-3-oxobutanoic ester represented by formula (I).

4. The process according to claim 1, wherein the ruthenium-optically active phosphine complex is selected from a compound represented by formula (IV):

   (IV)

wherein BINAP stands for 2,2'-bis(diphenylphosphino)-1,1'-binaphthyl; S represents a tertiary amine; y represents 0 or 1; when y is 0, x represents 2, z represents 4, and p represents 1; and when y is 1, x represents 1, z represents 1, and p represents 0, a compound represented by formula (V):

   (V)

wherein BINAP is as defined above; Y represents $ClO_4^-$, $BF_4^-$ or $PF_6^-$; l represents 0 or 1; when l is 0, v represents 1, and w represents 2 and when l is 1, v represents 2, and w represents 1, and a compound represented by formula (VI):

   (VI)

wherein BINAP is as defined above; S represents benzene which may be substituted with a straight-chain or branched lower alkyl group or a carboalkoxy group, or acetonitrile; X represents a halogen atom; Y represents a halogen atom, $ClO_4^-$, $BF_4^-$, $PF_6^-$ or $BPh_4^-$, wherein Ph represents a phenyl group; l represents 1 or 0; when l is 1, m represents 1, and n represents 1; and when l is 0, m represents 4, and n represents 2.

* * * * *